(12) United States Patent  
Seftel et al.

(10) Patent No.: US 8,917,965 B2  
(45) Date of Patent: Dec. 23, 2014

(54) LASER OPTICAL FIBER STORAGE

(76) Inventors: Allen D. Seftel, Cherry Hill, NJ (US); Andrew Robinson, Coventry, CT (US); Robert Morton, Suffield, CT (US); Christopher Floury, Warren, MA (US); Ronald George Litke, Jr., Sandy Hook, CT (US); Spencer William Shore, Hamden, CT (US)

( * ) Notice: Subject to any disclaimer, the term of this patent is extended or adjusted under 35 U.S.C. 154(b) by 130 days.

(21) Appl. No.: 13/577,781

(22) PCT Filed: Aug. 10, 2011

(86) PCT No.: PCT/US2011/047273  
§ 371 (c)(1),  
(2), (4) Date: Aug. 8, 2012

(87) PCT Pub. No.: WO2012/021636  
PCT Pub. Date: Feb. 16, 2012

(65) Prior Publication Data  
US 2013/0129297 A1 May 23, 2013

Related U.S. Application Data

(60) Provisional application No. 61/466,216, filed on Mar. 22, 2011, provisional application No. 61/372,150, filed on Aug. 10, 2010.

(51) Int. Cl.  
*G02B 6/00* (2006.01)  
*G02B 6/36* (2006.01)  
*A61B 18/22* (2006.01)  
*G02B 6/44* (2006.01)  
*A61B 19/02* (2006.01)  
*A61N 5/06* (2006.01)  
*A61B 19/00* (2006.01)

(52) U.S. Cl.  
CPC ........... *G02B 6/444* (2013.01); *A61N 2005/063* (2013.01); *A61B 2019/409* (2013.01); *A61B 18/22* (2013.01); *A61B 2019/267* (2013.01); *A61B 19/026* (2013.01); *A61B 2018/2205* (2013.01)  
USPC .......................................... 385/135; 385/147

(58) Field of Classification Search  
USPC ................................................. 385/135–137  
See application file for complete search history.

(56) References Cited

U.S. PATENT DOCUMENTS 4,775,211 A * 10/1988 Wondrazek et al. ............ 385/88  
4,952,012 A    8/1990 Stamnitz  
(Continued)

*Primary Examiner* — Akm Enayet Ullah  
(74) *Attorney, Agent, or Firm* — Howard M. Cohn; Daniel Cohn

(57) ABSTRACT

A laser optical fiber storage device (10,100) for temporarily storing a free end (12a) of an elongated flexible laser optical fiber (12). A storage housing (14,114) with an open end (116) has an elongated flexible tube (28,128) disposed therein to receive the elongated flexible laser optical fiber so as to prevent laser light from escaping the storage housing. A restrictor (32, 117a, 117b) within the storage housing reduces the inner diameter of the elongated flexible tube. Further, a laser optical fiber storage device (40,100) for temporarily storing a free end (12a) of an elongated flexible laser optical fiber (12) is provided with a clamp (42,123). The storage housing (41, 114) has an open end (41a, 116) and an elongated flexible tube (28,128) disposed within the storage housing to receive the elongated flexible laser optical fiber so as to prevent laser light from escaping the storage housing. A laser fiber clamp (42,123) is mounted to the open end to secure the laser optical fiber.

33 Claims, 12 Drawing Sheets

(56) References Cited

U.S. PATENT DOCUMENTS

| | | | |
|---|---|---|---|
| 5,219,650 A | | 6/1993 | Ritter |
| 5,263,585 A | | 11/1993 | Lawhon et al. |
| 5,269,777 A | * | 12/1993 | Doiron et al. ............. 606/7 |
| 5,402,508 A | * | 3/1995 | O'Rourke et al. ......... 385/31 |
| 5,873,865 A | | 2/1999 | Horzewski et al. |
| 6,144,791 A | | 11/2000 | Wach et al. |
| 6,840,238 B1 | | 1/2005 | Van Hegelsom |
| 7,672,713 B2 | * | 3/2010 | Furnish ................. 600/476 |
| 7,956,317 B2 | * | 6/2011 | Artyushenko ......... 250/227.24 |
| 8,477,298 B2 | * | 7/2013 | Sutherland ............ 356/138 |
| 8,594,478 B2 | * | 11/2013 | Seftel et al. ............ 385/135 |
| 2006/0064080 A1 | | 3/2006 | Cao |
| 2008/0181261 A1 | | 7/2008 | Boutoussov et al. |
| 2008/0183163 A1 | | 7/2008 | Lampropoulos et al. |
| 2009/0275930 A1 | | 11/2009 | Di Sessa et al. |
| 2010/0004642 A1 | | 1/2010 | Lumpkin |

\* cited by examiner

LASER OPTICAL FIBER STORAGE

CROSS-REFERENCE TO RELATED APPLICATIONS

This application claims the benefit of U.S. Provisional Patent Application No. 61/466,216 entitled "LASER FIBER CLAMP" filed on Mar. 22, 2011, and of U.S. Provisional Patent Application No. 61/372,150 entitled "APPARATUS FOR STORING A LASER OPTICAL FIBER" filed on Aug. 10, 2010 which is hereby expressly incorporated herein by reference.

TECHNICAL FIELD OF THE INVENTION

The invention relates to laser optical fiber storage and more particularly to a method and device for storing a laser optical fiber with an associated clamp whereby laser light generated by the accidental discharge of the laser will not escape the laser optical fiber storage device.

BACKGROUND OF THE INVENTION

Surgical laser devices or systems supply energy from a laser source, through such energy delivery systems as laser optical fiber delivery systems or waveguides like articulated arms, to the tissue of a patient. In a number of cases, a probe is connected to the distal end of the energy delivery system to facilitate the delivery of concentrated therapeutic energy to the tissue being treated.

Storage devices to house and dispense surgical catheters are well known in the art. These devices generally provide a protective covering for fragile and expensive surgical catheters. Some such devices highlight a storage function; others are specialized to dispense the encased catheter during an operation; still others are designed to perform both functions. Moreover, such devices can be designed to house a variety of different catheter types.

Laser devices or systems that have been designed for use in contact with tissue generally include a fiber optical cable affixed to a laser energy delivery system. Such devices offer a number of advantages over free-beam energy delivery systems: they significantly reduce the waste arising from the backscatter of laser energy from the tissue; they define a clear and precise area of irradiation; they protect the laser optical fiber or other energy delivery system from fouling; and they provide tactile feedback to the surgeon. Perhaps most importantly, the probe may be treated to absorb or scatter laser energy, or both, such that both radiated photonic energy and conducted thermal energy can be delivered to the tissue.

Surgical laser devices or systems supply energy from a laser source, through such energy delivery systems as fiber optical delivery systems or waveguides like articulated arms, to the tissue of a patient. In a number of cases, a probe is connected to the distal end of the energy delivery system to facilitate the delivery of concentrated therapeutic energy to the tissue being treated. From a general perspective, surgical laser devices or systems may be divided into two categories: those that are designed for use in contact with tissue, and those that are designed for use without contact with tissue.

ASPECTS OF THE INVENTION

An aspect of the present invention includes providing an improved method and device for suitable, cost effective temporary storage and dispensing of surgical laser optical fibers.

Another further aspect of the present invention is to provide a device that is able to resist burn-through by a medical laser beam for at least a desirable time interval.

A further aspect of the present invention is to provide a safety mechanism to protect the patient and the hospital staff from inadvertent firing of the optical laser optical fiber.

A still further aspect of the present invention is to protect a non-laser delivery system, such as a ureteroscope, during a procedure or surgery.

A yet further aspect of the present invention is to provide a device that maintains the sterility of a laser optical fiber during a procedure.

Another aspect of the present invention is to provide a cost effective system that reduces the chance for needing additional fibers during use or during a procedure.

Another aspect of the present invention is to provide a tube, such as a silicone tube, within a device into which a surgical laser optical fiber can be inserted and that is able to resist burn-through by a medical laser beam for at least a desirable time interval.

SUMMARY OF THE INVENTION

A laser optical fiber storage device for temporarily storing a free end of an elongated flexible laser optical fiber includes a storage housing having an open end. An elongated flexible tube, preferably constructed of silicone rubber is disposed within the storage housing to receive the elongated flexible laser optical fiber so as to prevent laser light from escaping the storage housing. A restrictor within the storage housing reduces the inner diameter of the elongated flexible tube.

Further, a method is disclosed for temporarily storing a free end of an elongated flexible laser optical fiber. This method comprises providing a storage housing having an open end, disposing an elongated flexible tube within the storage housing, inserting the free end of the elongated flexible laser optical fiber into the elongated flexible tube so as to prevent laser light from escaping the storage housing, and reducing the inner diameter of the elongated flexible tube to engage the free end of the optical fiber.

Further disclosed is a laser optical fiber storage device for temporarily storing a free end of an elongated flexible laser optical fiber. The device includes a storage housing having an open end, an elongated flexible tube disposed within the storage housing adapted to receive the elongated flexible laser optical fiber so as to prevent laser light from escaping the storage housing, and a laser fiber clamp mounted to the open end adapted to secure the laser optical fiber.

A further method is disclosed for temporarily storing a free end of an elongated flexible laser optical fiber. This method comprises providing a storage housing having an open end, securing an elongated flexible laser optical fiber within a laser fiber clamp, and mounting the laser fiber clamp to the open end of the storage housing, whereby the elongated flexible laser optical fiber is disposed within the storage housing so as to prevent laser light from escaping the storage housing.

DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

If shading or cross-hatching is used, it is intended to be of use in distinguishing one element from another (such as a cross-hatched element from a neighboring un-shaded element. It should be understood that it is not intended to limit the disclosure due to shading or cross-hatching in the drawing figures.

Figure 1:
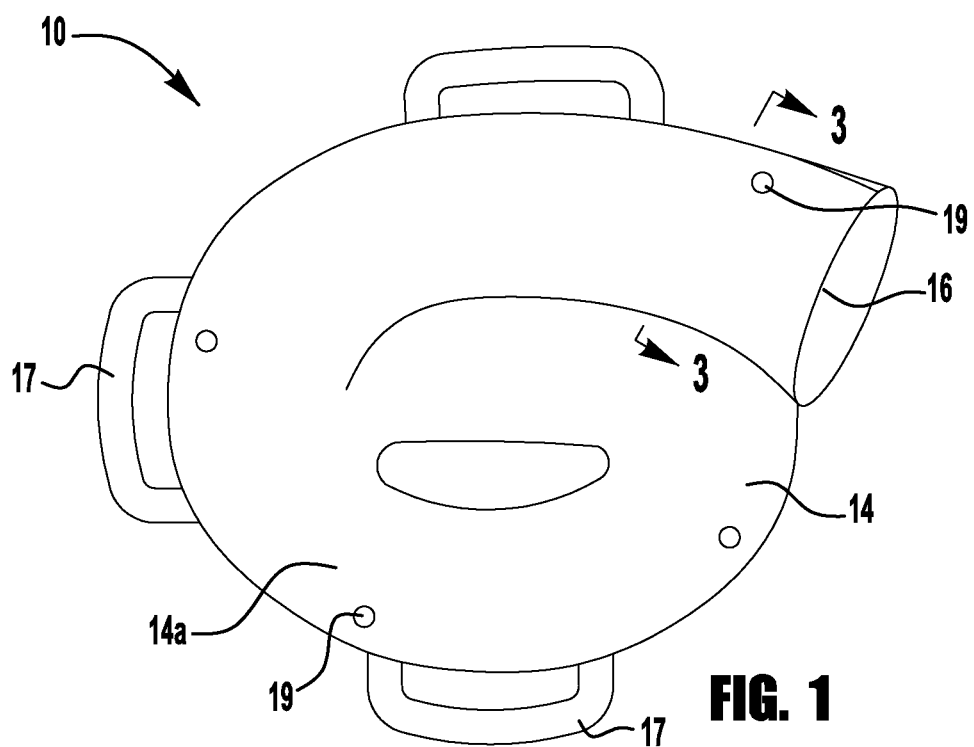

In the drawings accompanying the description that follows, both reference numerals and legends (labels, text descriptions) may be used to identify elements. If legends are provided, they are intended merely as an aid to the reader, and should not in any way be interpreted as limiting.

FIG. 1 shows a side, three-dimensional view of the device for storing a laser optical fiber, according to the present invention.

Figure 2:
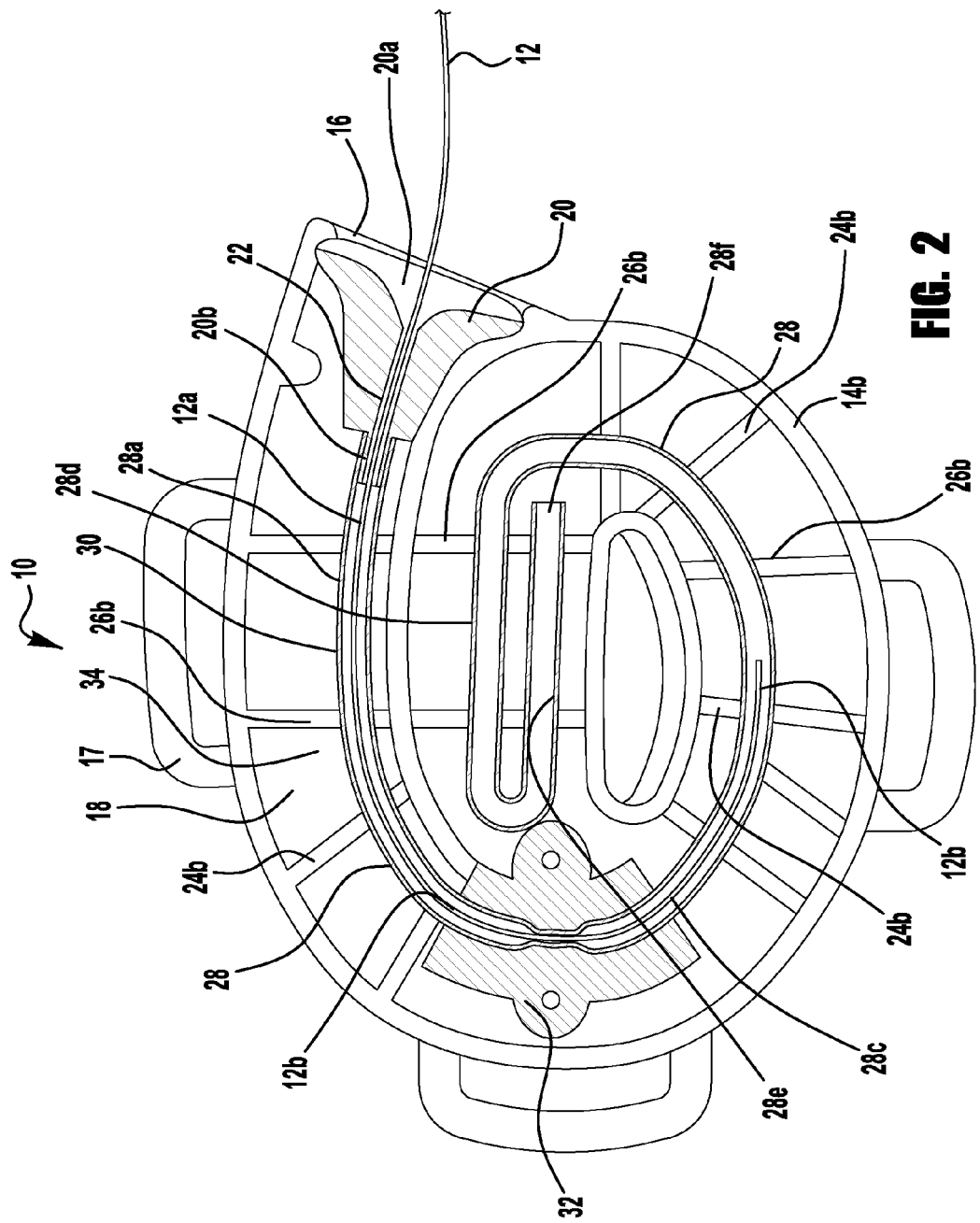

FIG. 2 shows a side, cross-sectional view of the device for storing a laser optical fiber, according to the present invention.

Figure 3:
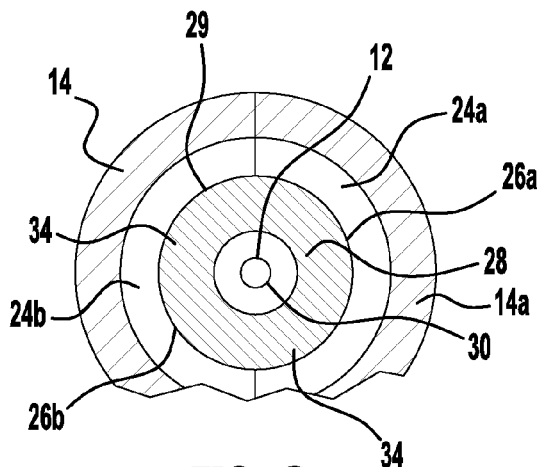

FIG. 3 is a view through 3-3 of FIG. 1, according to the present invention.

Figure 3A:
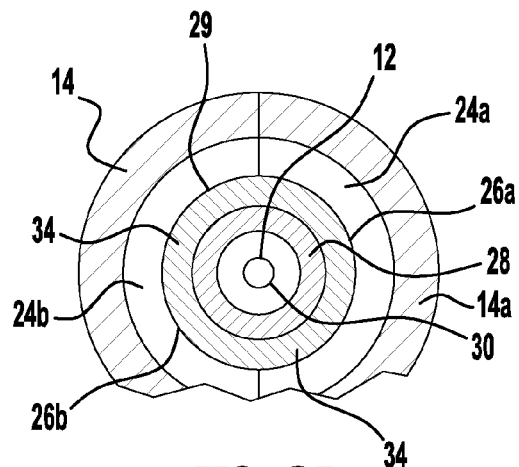

FIG. 3A is an alternative embodiment showing a view through 3-3 of FIG. 1, according to the present invention.

Figure 4:
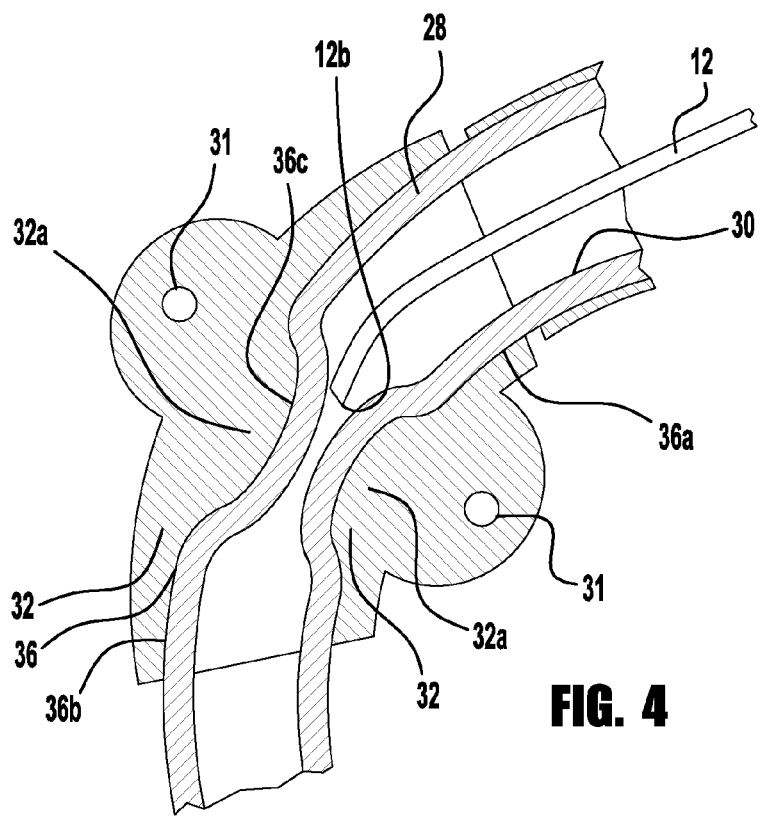

FIG. 4 shows a side, cross-sectional view of a restrictor element designed for use with the device for storing a laser optical fiber, according to the present invention.

Figure 5:
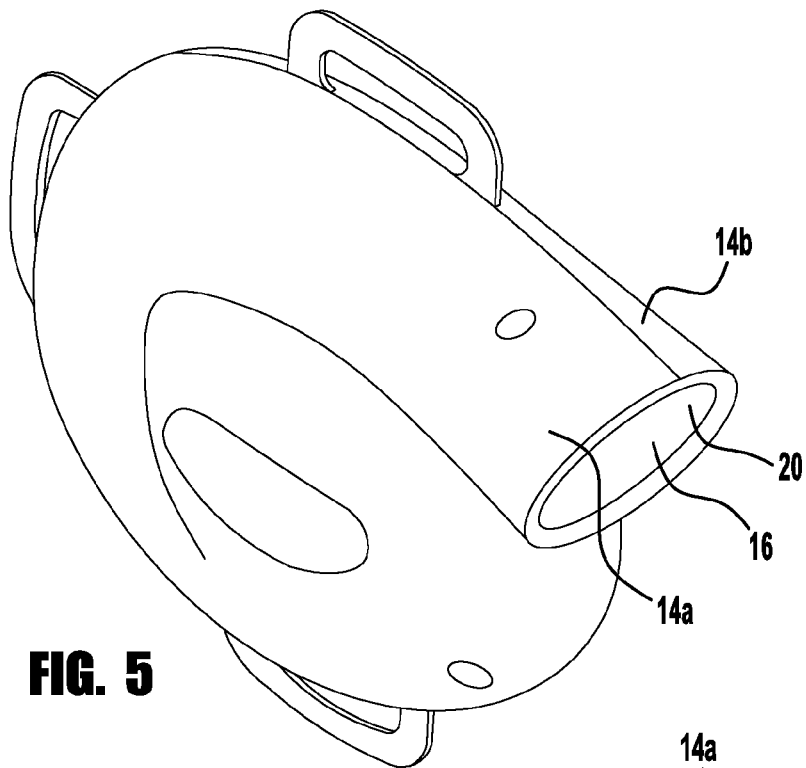

FIG. 5 shows a three-dimensional view of the device for storing a laser optical fiber, according to the present invention.

Figure 6:
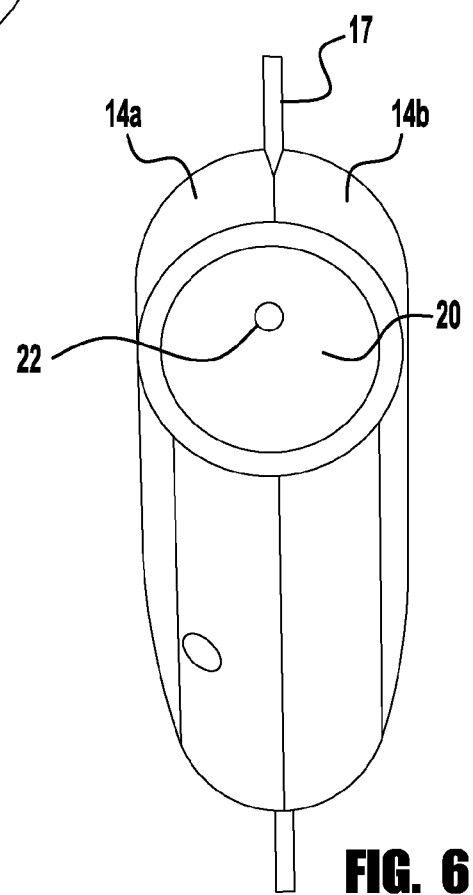

FIG. 6 shows a front, three dimensional view of the device for storing a laser optical fiber, according to the present invention.

Figure 7:
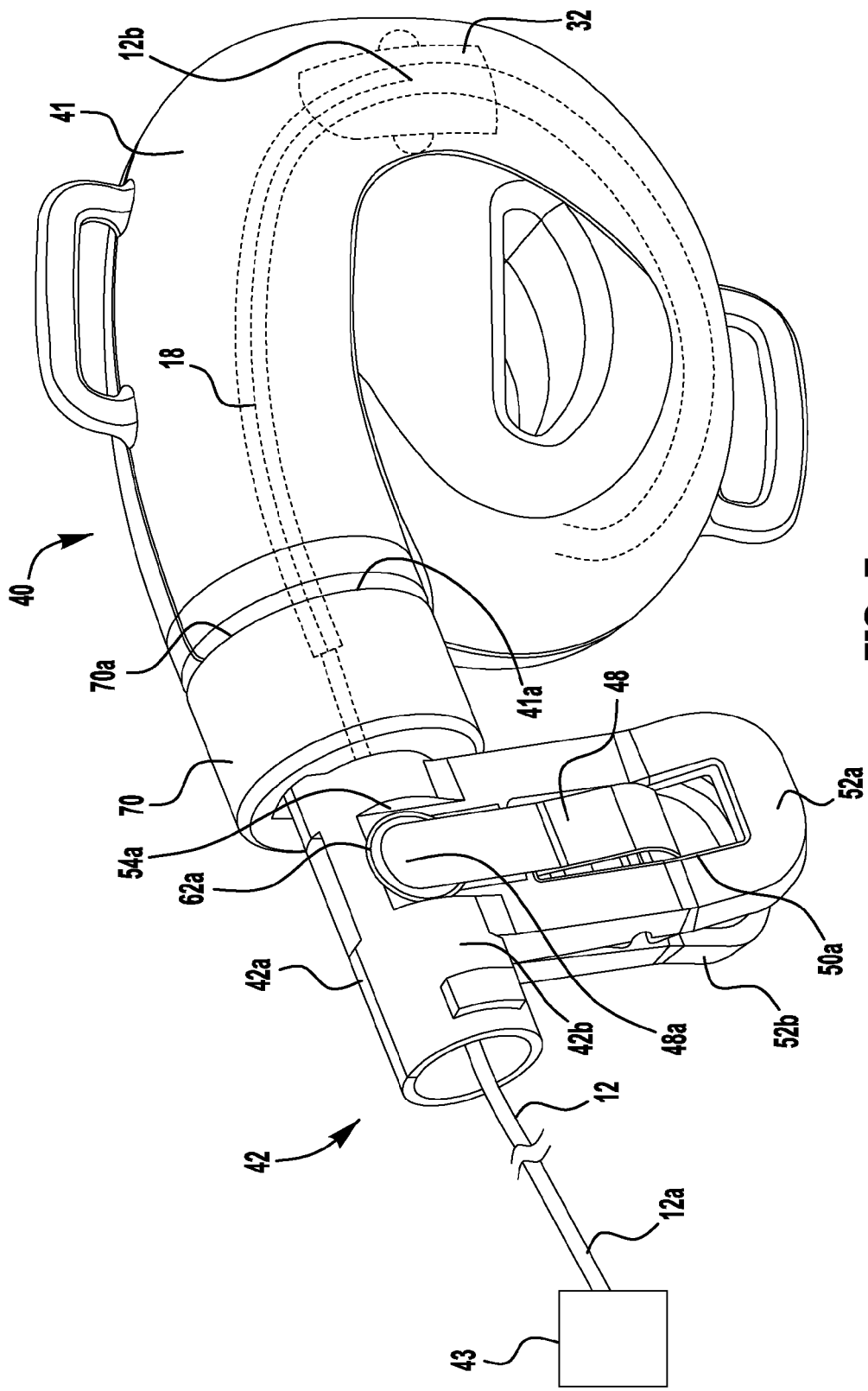

FIG. 7 shows a side, three-dimensional view of the laser optical fiber clamp in use with the device for storing a laser optical fiber, according to the present invention.

Figure 8:
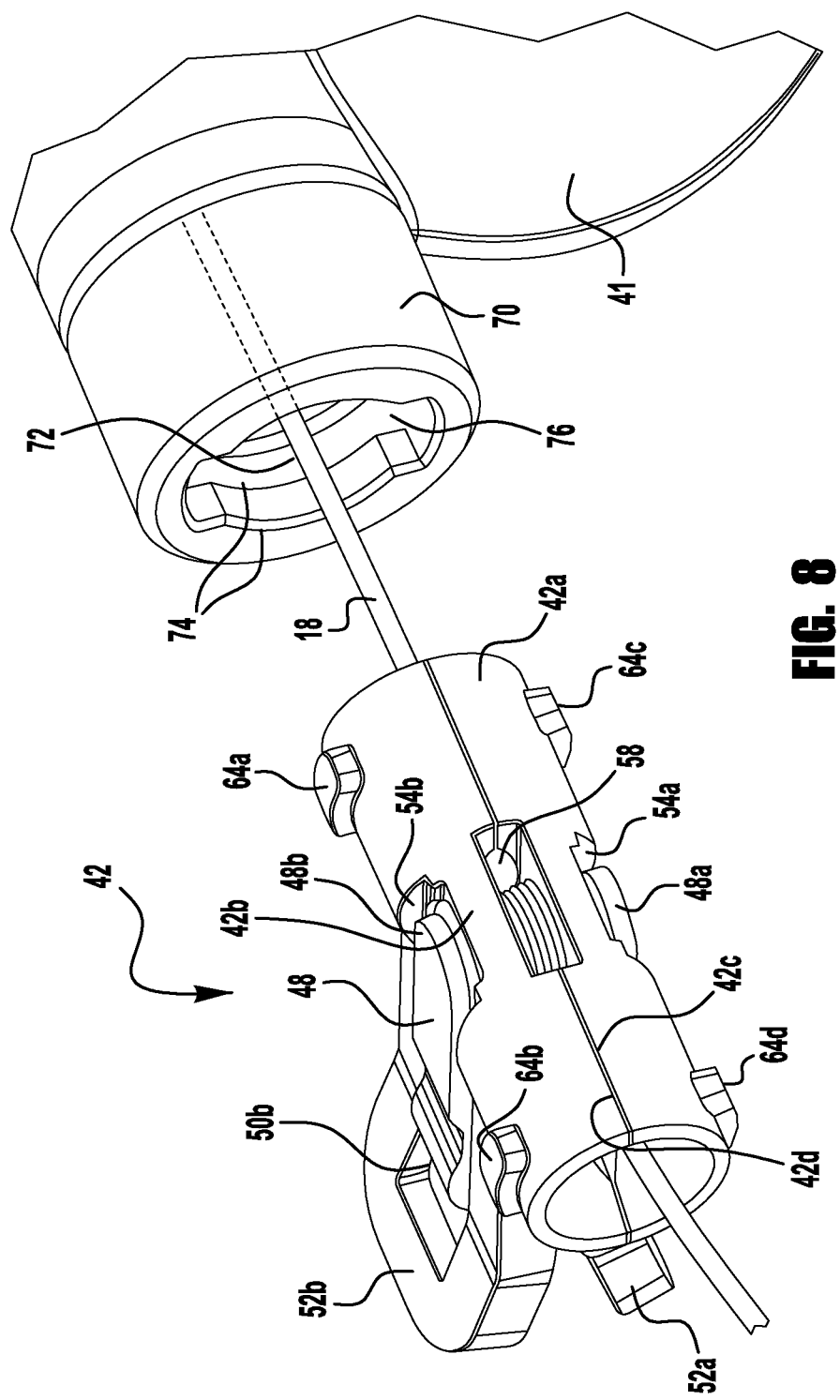

FIG. 8 shows a side, three-dimensional view of the laser optical fiber clamp and the front insert for mounting the clamp to the device for storing a laser optical fiber, according to the present invention.

Figure 9:
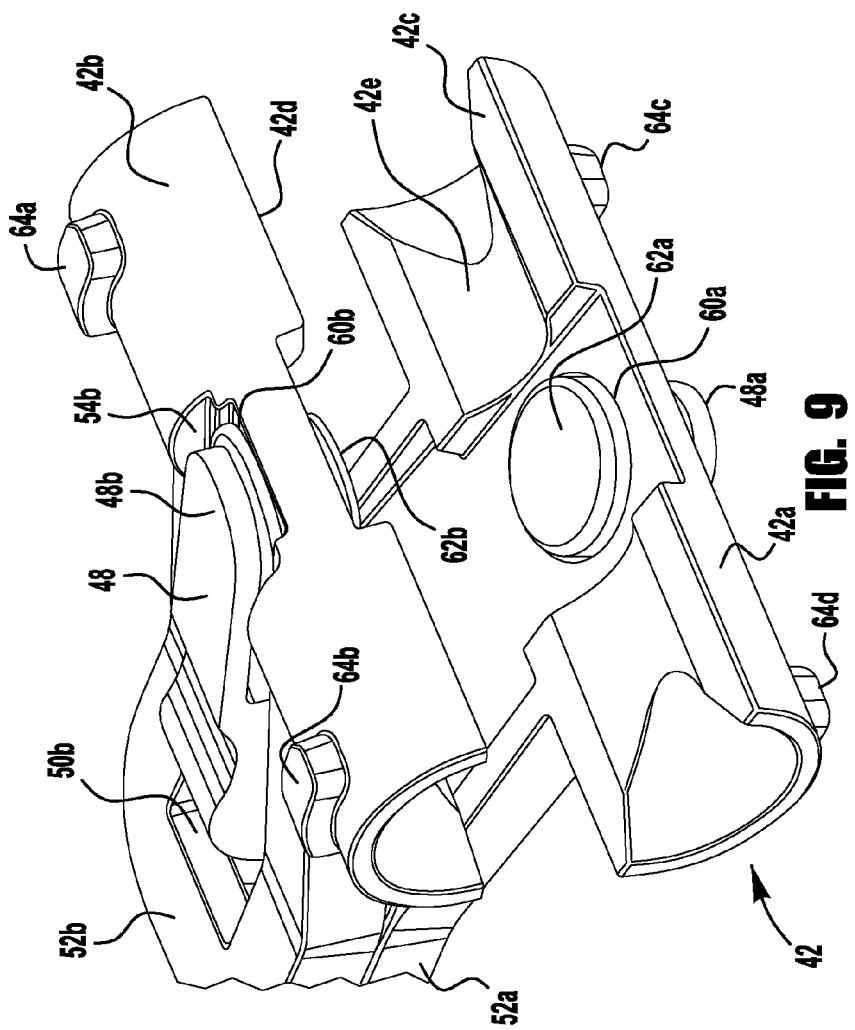

FIG. 9 shows a side three-dimensional view of the laser optical fiber clamp in the open position, according to the present invention.

Figure 10:
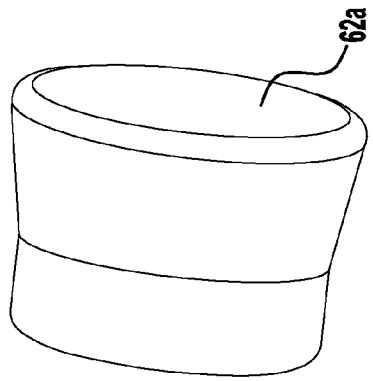

FIG. 10 shows a front three-dimensional view of the rubber tab of the laser optical fiber clamp, according to the present invention.

Figure 11:
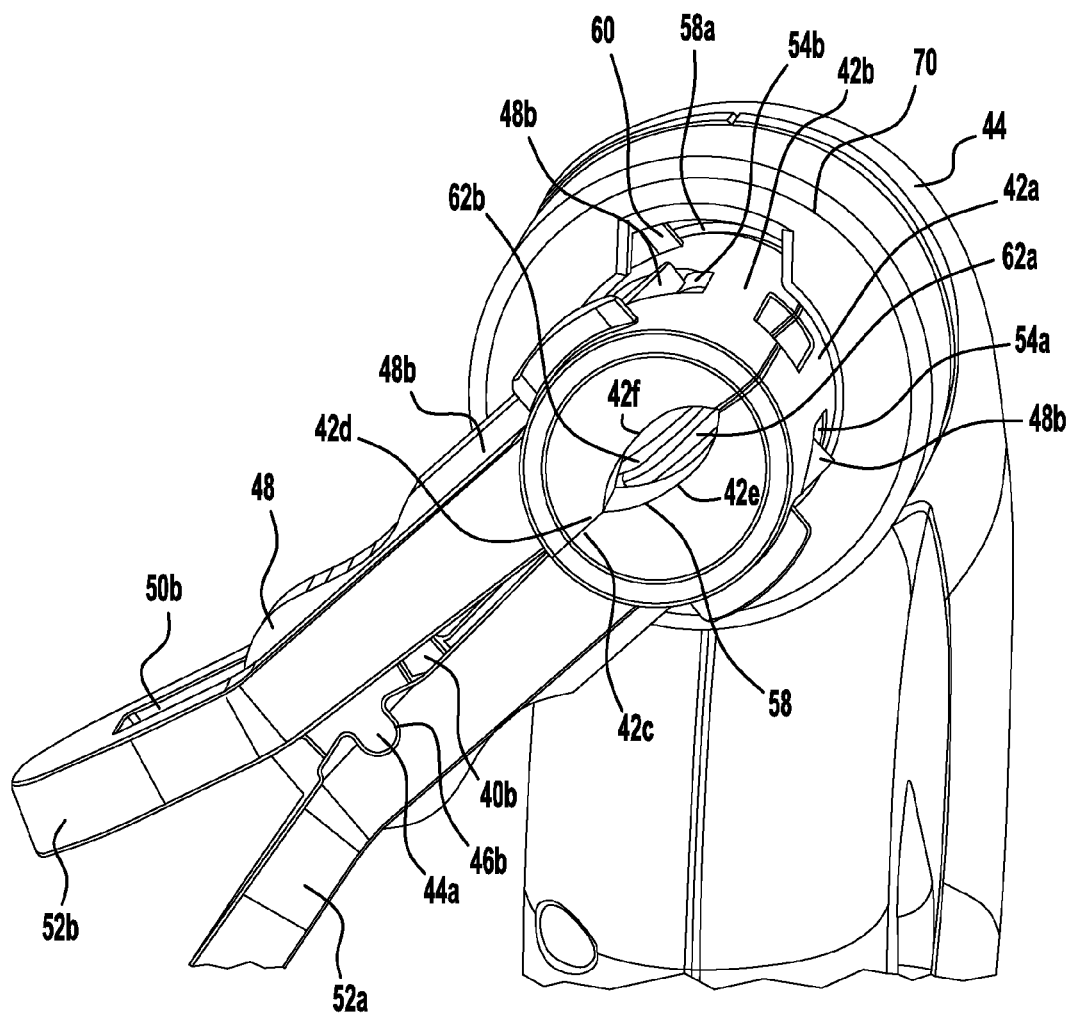

FIG. 11 shows a side view, cross-sectional view of the laser optical fiber clamp engaged in the front insert of the device for storing a laser optical fiber, according to the present invention.

Figure 12:
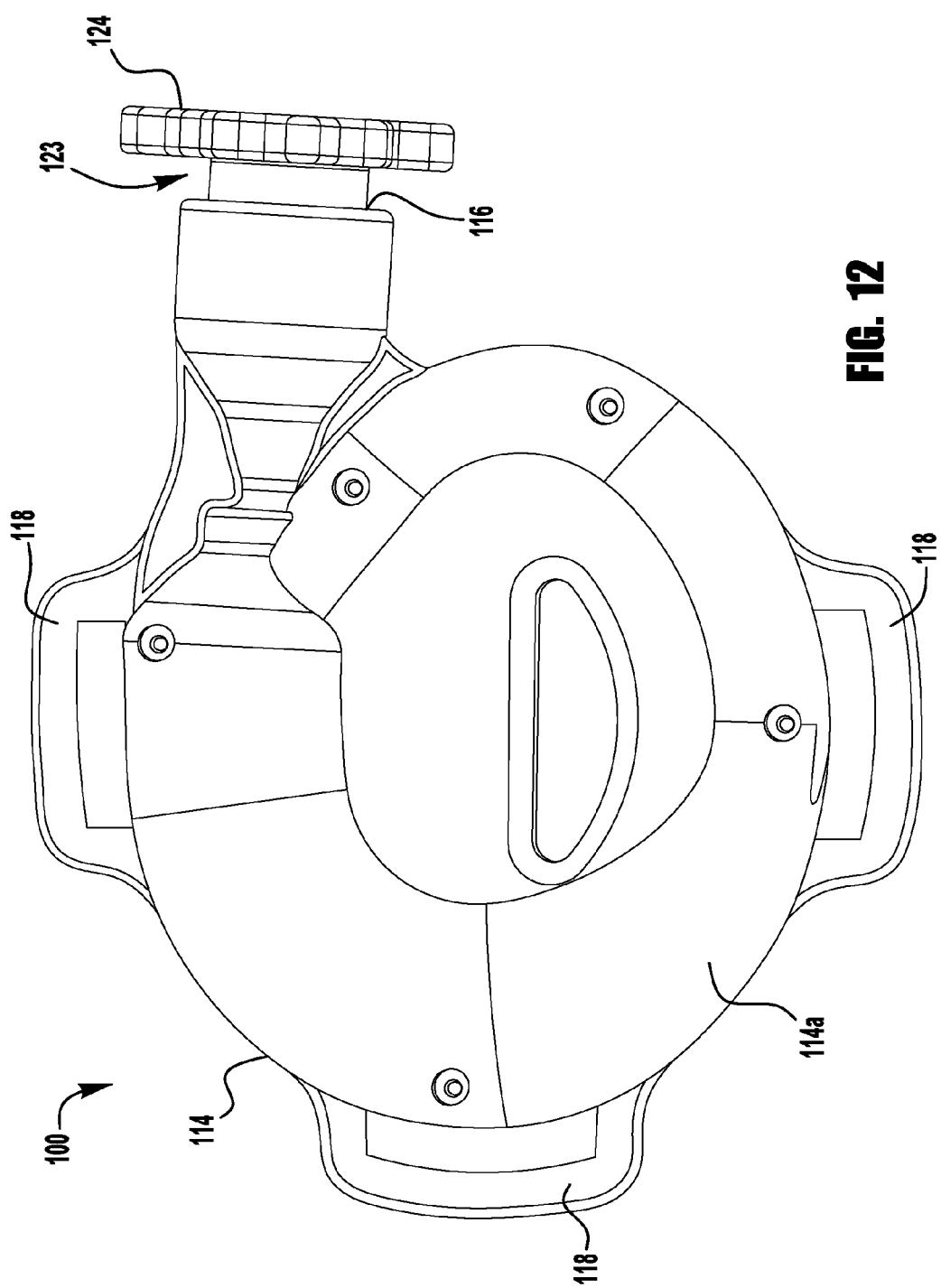

FIG. 12 shows a side, three-dimensional view of an alternative embodiment of the device for storing a laser optical fiber, according to the present invention.

Figure 13:
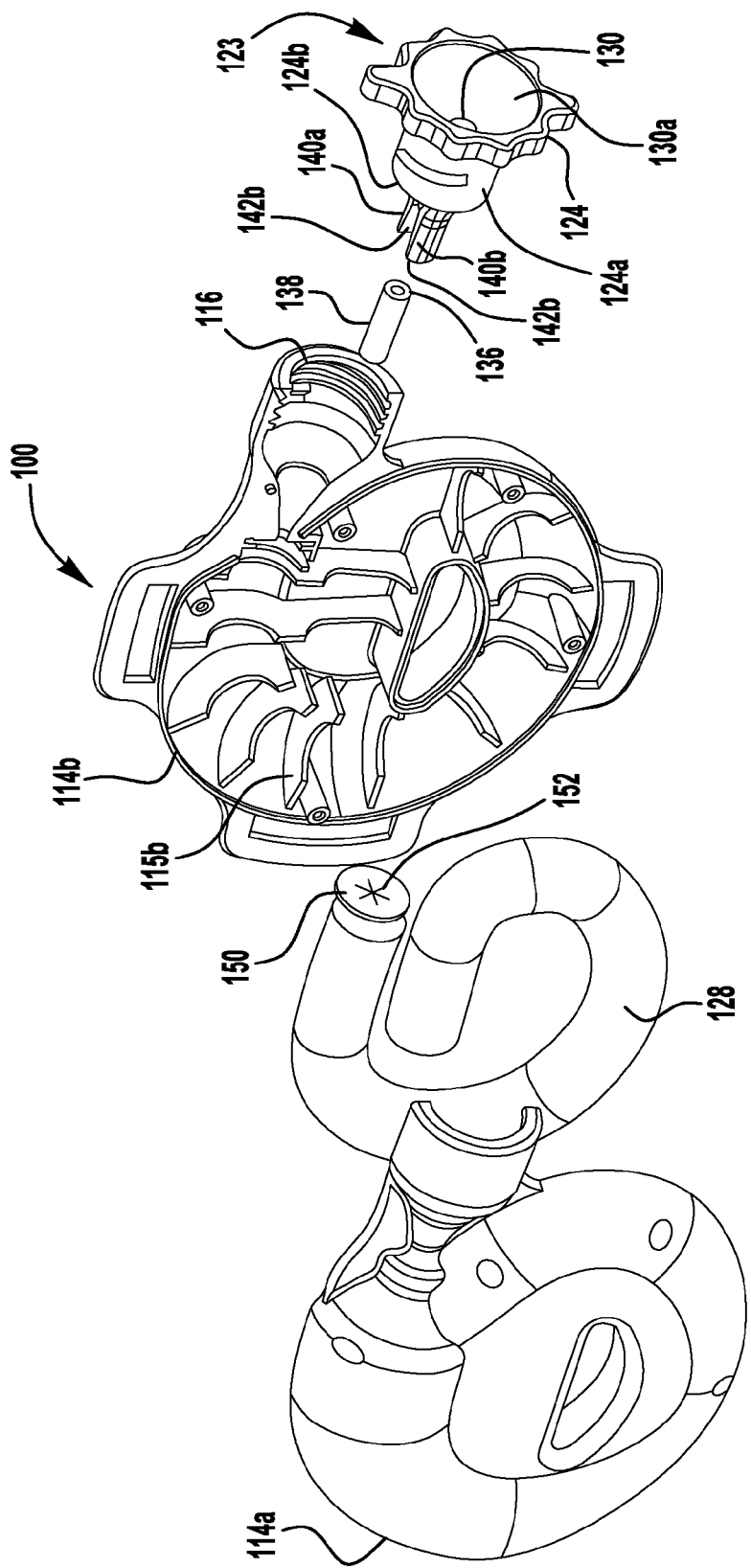

FIG. 13 shows an exploded view the alternative embodiment of the device for storing a laser optical fiber, according to the present invention.

Figure 14:
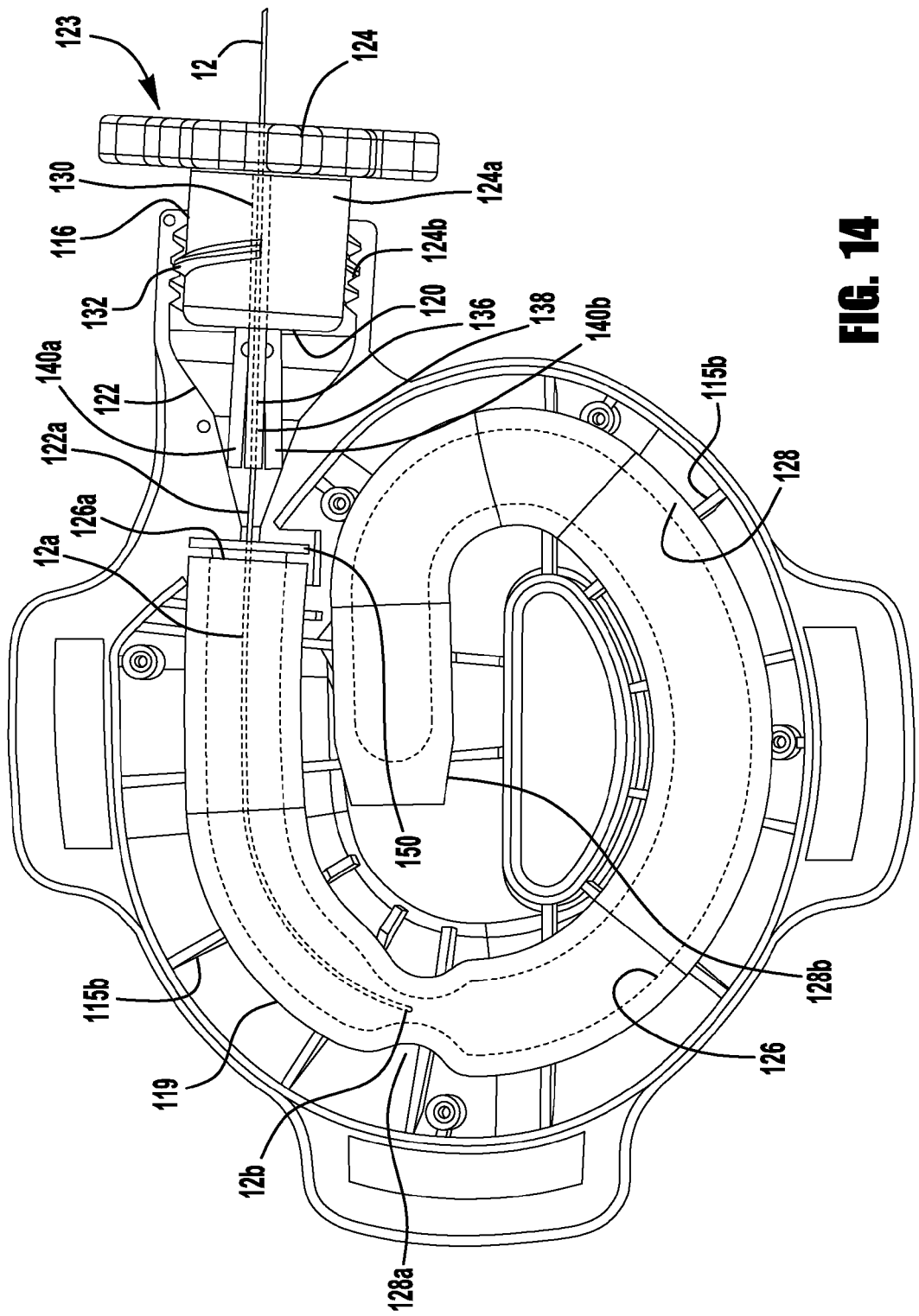

FIG. 14 is a side view showing one side of the alternative embodiment of the device for storing a laser optical fiber, according to the present invention.

Figure 15:
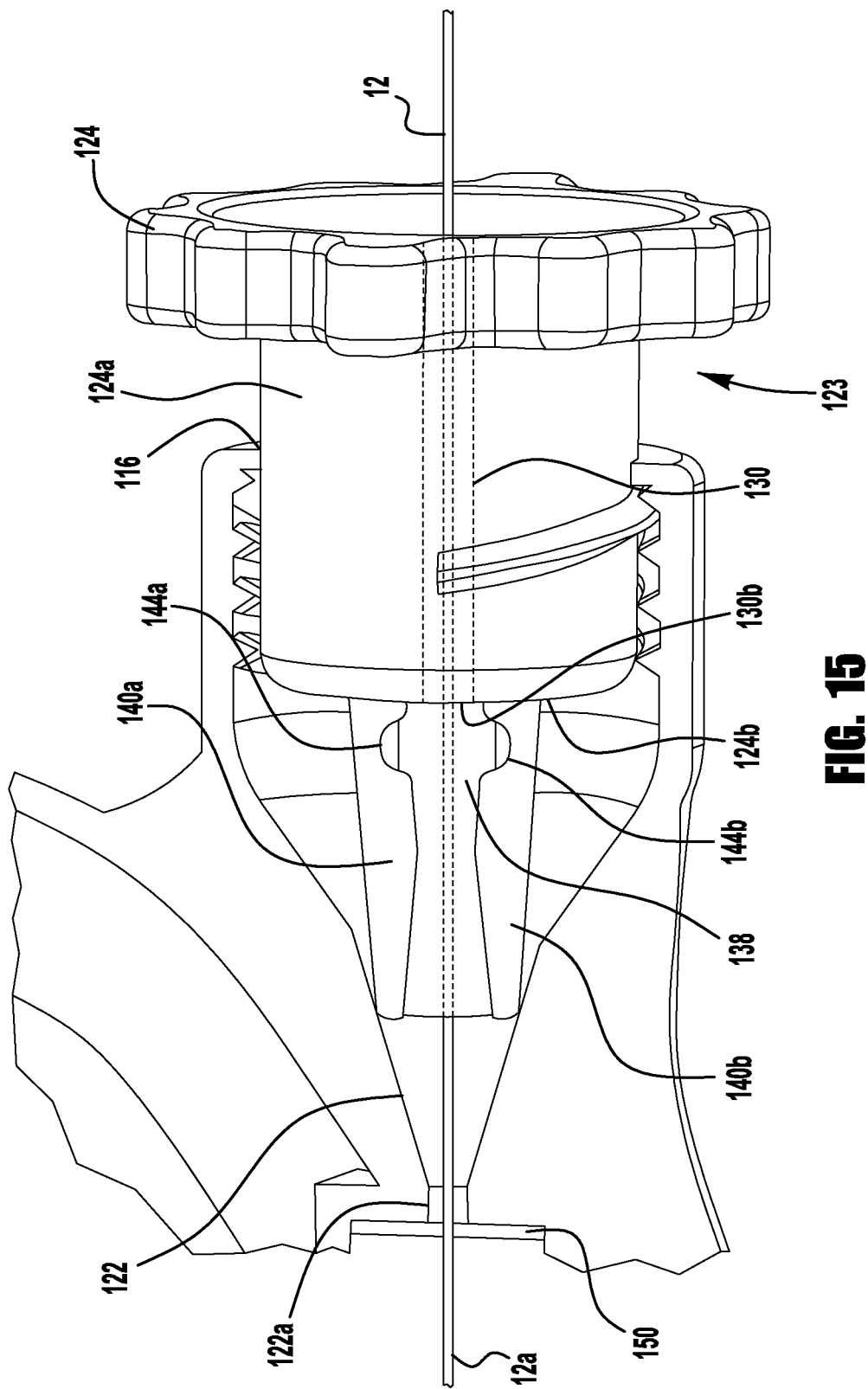

FIG. 15 is a side view the entrance of the alternative embodiment of the device for storing a laser optical fiber, according to the present invention.

DESCRIPTION OF THE PREFERRED EMBODIMENTS

In the description that follows, numerous details are set forth in order to provide a thorough understanding of the present invention. It will be appreciated by those skilled in the art that variations of these specific details are possible while still achieving the results of the present invention. Well-known processing steps and materials are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

Referring to FIGS. 1 and 2, there is shown a device 10 for temporarily storing a laser optical fiber 12 (hereafter "device"). Device 10 is designed as laser optical fiber storage system for temporarily storing a free end section 12a of the elongated flexible laser optical fiber 12. Device 10 includes a storage housing 14 having an open end 16. By temporarily disposing the free end 12a of laser optical fiber 12 in storage housing 14, the free end is protected from any potential source of contamination or potential breakage, and any accidentally discharged laser light from the laser optical fiber is safely contained within the storage housing. Device 10 is preferably designed to be used during a medical procedure where a physician is using an laser optical fiber connected to a laser source (not shown) for emitting laser radiation. Device 10 may either be designed to be a one-use instrument, or to be sterilized and used a multitude of times. While the device 10 is preferably used during a medical procedure, it is within the terms of the invention to use it for safeguarding a laser optical fiber in any type of environment.

There are a number of ring shaped protrusions 17 that can be attached to the top, side, and bottom of device 10. Rings 17 are used to attach device 10 to a patient, by means of a Velcro strap, flexible elastic, two-sided adhesive, or any other suitable attachment means. While device 10 is generally designed to be attached to the patient's leg, it is within the terms of the present invention to attach device 10 to any other part of the patient's body or to a non-patient site in proximity to the sterile or surgical field.

The device 10 is preferably constructed as a housing 14 with an open end 16. The storage housing 14 can be formed of two hollow storage housing sections 14a and 14b, which are the mirror image of each other. When housing sections 14a and 14b are joined together as indicted in FIGS. 1, 2 and 5, they form the spiral shaped channel 18. While screws 19 are indicated as the means to join the housing sections 14a and 14b together, it is within the terms of the invention to join them in any desirable way, such as with an adhesive. The storage housing 14 can be constructed of a variety of materials, such as but not limited to, for example, plastic, silicone, polymers and aluminum.

The open end 16 of housing 14 receives a funnel 20 having a passageway 22 extending therethrough. One end of the passageway 22 forms a wide mouth 20a while the opposite end of the passageway is aligned with the passageway 30 through elongated flexible tube 28. One end of tube 28 can be attached to the end of the funnel 20 disposed within the housing 14 by any desired means, such as but not limited to, providing a cylindrical end connector extending from the end of the funnel opposite from the wide mouth, onto which the passageway 30 of the elongated flexible tube 28 can be forced thereon. The material of the funnel 20 is designed to be laser energy impermeable, as with the rest of housing 14. All of the plastic components are preferably heat resistant, but not necessarily impermeable to laser energy.

The inner passageway 22 through funnel 20 aligns with the passageway 30 through tube 28. In an exemplary tube 28, the passageway 30 of tube 28 has a diameter of about 1.7 cm, an inner diameter of about 0.1 cm to about 1 cm and the wall thickness of the tube can be about 0.3 cm to about 1 cm. These dimensions as described do not preclude the use of other suitable dimensions.

Referring to FIG. 2, there is shown one side 14b of the storage housing 14. As shown in FIG. 5, the housing 14 includes two opposite mating sections 14a and 14b that form the receptacle or storage housing 14 for temporarily storing free end section 12a of the elongated flexible laser optical fiber 12. The elongated fiber 12 is inserted within the storage housing 14 through the passageway 22 extending through the funnel 20. The wide mouth 20a of the funnel guides the distal end 12b of laser optical fiber 12 into the elongated rubber tube 28 which is disposed, preferably in a spiral configuration, within the storage housing 14. Housing 14 is configured to insert and retain the free end section 12a of the laser optical fiber 12 in a coiled configuration within silicone rubber tube 28 so as to enable the complete removal of the free end section of the laser optical fiber there from.

There are a plurality of spaced ribs 24b that extend from mating side section 14b, as shown in FIG. 2, and a matching plurality of spaced of ribs 24a (see FIG. 3) extending outward from the inner side of side section 14a. Each of the ribs 24a and 24b has a semi-circular cutout 26a (not shown) and 26b, respectively, sized to accommodate the tube 24, described hereinafter, so when the two sides 14a and 14b are secured together, the tube 28 is enclosed by a circular openings 29 (see FIG. 3) formed by semicircular cutouts 26a and 26b formed when the matching pairs of ribs 24a and 24b engage each other. The circular openings 29 form a spiral shaped pathway to configure the elongated flexible tube 28 in a coiled configuration.

The ribs 24a and 24b also function to position the tube 28 in the storage housing 14. Referring to FIG. 2, the ribs 24a and 24b force the tubing 28 to spiral around within the housing 14 from the cylindrical stem 20b of the funnel 20 so that the inner diameter of the passageway 30 through the tube 28 is aligned with the passageway 22. The passageway 22 can have a smaller diameter then that of the tube passageway 30 so that when the distal end 12b of the elongated fiber 12 is fed through the passageway 22 and into the tube passageway 30, it will easily move into and through the passageway 30.

The elongated flexible tube 28 is selected to be substantially non-burnable when exposed to a medical laser beam fired through the laser optical fiber 12. Moreover, the tube 28 is able to resist burn-through when exposed to a medical laser beam for at least a desirable time interval of about 1 second to about five minutes.

While elongated flexible tube 28 can be constructed of any desirable material able to resist burn-through when exposed to a medical laser beam for at least the desirable time interval, a preferred material is silicone, such as platinum cured silicone rubber tubing.

A first portion 28a of the tube 28 extends between the cylindrical stem 20b of funnel 20 and the restrictor 32 (later described). The first portion 28a of the tubing 28 can have a thicker wall than the remainder of the tube 28. This thicker wall may formed by an additional tube 34 that surrounds tube 28, as shown in FIG. 3A. Alternatively, portion 28a may be formed by over molding to create a thicker wall portion of tube 28a as shown in FIG. 3. Of course, in the portion 28a, the tubular passageway 30 remains the same diameter as through the remainder of tube 28.

The purpose of forming at least portion 28a of the tube 28 with a larger wall thickness is to prevent burn through from the laser light emitted from a side-fire type laser optical fiber 12. Being that a side fire laser optical fiber is generally of a larger diameter than conventional laser optical fibers that emit the laser beam directly out of the end of the fiber, the side-fire type laser optical fiber 12 will tend to be caught when it encounters the section of the tube 30 disposed within the restrictor 32, as discussed hereinafter.

Referring to FIG. 4, there is shown elongated flexible tube 28 extending through the restrictor 32. Restrictor 32 may disposed within the storage housing 14 in the area where the tubing 28 bends back on itself as shown in FIG. 2. The restrictor 32 can be attached to the storage housing 14 by a variety of means, including screws through holes 31 on either side of the restrictor. Restrictor 32 has an inner bore 36 that is sized to receive the tube 28. The cylindrical sections 36a and 36b of inner bore 36 at opposite sides of the restrictor 32 are generally circular and have a diameter corresponding to the outer diameter of tube 28. In a central section 32a of restrictor 32, the central section 36c of inner bore 36 necks down so that the diameter of tube 28 and the inner diameter of the passageway 30 through tube 28 are both reduced in the central section 32a, as shown in FIG. 4.

While a restrictor 32 has been illustrated, it is within the terms of the invention to use the ribs 24a and 24b to squeeze the tube 28. This could be accomplished by creating a section of the opening 29 formed by the pair of cutouts 26a and 26b in one or more adjacent pairs of matching ribs 24a and 24b. In this embodiment, the elongated flexible tube 28 would be squeezed into a smaller diameter in the section where the reduced diameter of the opening 29 formed by the pair of cutouts 26a and 26b in the one or more pairs of matching ribs 24a, 24b when the two halves 14a and 14b of the housing 14 are assembled with the elongated flexible tube 28 in place within one half 14a or 14b of the housing 14.

The purpose of reducing the inner diameter of the tubing 28 with restrictor 32 is to catch the end 12b of a larger laser optical fiber 12 extending through the cylindrical section 36a as generally shown in FIG. 4. Stopping the end 12 in the necked down section of the tube 28 ensures that if a side fire laser optical fiber accidentally misfires, light will only be directed to the thicker section 28a of the tube 28 so that no laser light will escape from the housing 14. With a laser optical fiber 12 having a smaller diameter, the fiber will more easily pass through the necked down section of the tube and continue on down the tube as described hereinafter.

Referring again to FIG. 2, a section 28c of the tube 28 continues past restrictor 32 wraps around the inner periphery of housing 14 and extends in the general direction of opening 16 of the housing. Then, due to the placement of the ribs 24a, 24b, a section 28d of the tube is turned back in the direction of the restrictor 32. Finally, the end of section 28e of the tube 28 extends is in the direction of the opening 16 and can be closed by any means such as a plug (not shown) or by folding the tube back on itself.

When a thinner optical filament passes through restrictor 32, it is possible that it will go as far as the end section 28e. In the event of an accidental discharge of laser light, the light will not be go through the closed end 28f and therefore, the laser light will not escape from the housing 14.

Additional views of the housing 14 are shown in FIG. 5 which is a three-dimensional view of the housing 14, and FIG. 6 is a side view of the housing and FIG. 6 which is a bottom view of the housing.

A further embodiment of the device 40 (similar to device 10) is displayed in FIG. 7, which is a side three-dimensional view of a laser optical fiber clamp 42 in use with a storage housing 41 (similar to housing 14). The purpose of laser optical fiber clamp 42 is to ensure that laser optical fiber 12 remains in place within the storage housing 41 during the use of the device 40 in the midst of a surgical procedure. The clamping mechanism of laser optical fiber clamp 42 prevents movement of a clamped laser optical fiber 12 by a pulling force of between two and five pounds.

During a medical procedure, a laser optical fiber, such as laser optical fiber 12, is secured at one end 12a to a laser energy source 43. The opposite end 12b of the laser optical fiber is typically connected to a surgical instrument (not shown). However, when the free end 12b of laser optical fiber 12 is disconnected from the surgical instrument, while the opposite end 12a is still secured to the laser energy source 43, the free end 12b is loose and free to move about during surgical procedures. This freedom of movement can easily lead to the laser optical fiber 12 being broken or losing its sterility. Further, as discussed hereinbefore, the free laser optical fiber 12 can cause a significant injury to a patient or medical personnel in the event that the laser optical fiber is accidently fired off.

Presently, there is no device in the medical market designed to secure the free end of an laser optical fiber, which is attachment to a laser energy source, so that it is not prone to breakage, becoming unsterile or causing injury to a patient, medical personnel or to some device in the operating room. It would be desirable to secure the free end 12b of laser optical fiber 12 at some location so that the movement of the free end can be controlled. The combination of the storage housing 41 and the laser optical fiber clamp 42 alleviates this issue, as it can be secured at any location on the laser optical fiber 12 to thereby stabilize the fiber and prevent its movement from storage housing 41. This stabilization of laser optical fiber 12 is of great benefit to medical personnel conducting the surgical procedures.

Laser optical fiber clamp 42 is preferably constructed of plastic polymer. Similarly to the device 10, laser optical fiber clamp 42 has the ability to protect the patient and medical personnel should there be an accidental misfiring of the laser optical fiber 12 through a section of the fiber disposed within clamp. Although laser optical fiber clamp 42 as illustrated in the present embodiment is effective for securing a laser optical fiber 12 at any location along the length of the laser optical fiber and is designed to limit the movement of a laser optical fiber 12, it is also within the terms of the invention to incorporate the a clamp of any forms and or design with the storage housing 41.

Referring to FIGS. 8 and 11, there is shown a detailed view of the components of laser optical fiber clamp 42. There are two identical clamping sections, 42a and 42b that are aligned so that when the laser optical fiber clamp 42 closes, it can secure a laser optical fiber 12 as shown in FIG. 7. Each clamping section 42a and 42b has one projection 44a and 44b (not shown), respectively, (as seen in FIG. 11), having a curved surface that is pivotally disposed in the opposite clamping sections grooved receptacles 46a (not shown) and 46b so that the clamping sections can pivot about the grooved receptacles.

When the two clamping sections 42a and 42b are secured together so that the projections 44a and 44b are disposed within the grooved receptacles 46a and 46b, he two clamping sections 42a and 42b are then pivotally secured together by a generally u-shaped spring 48. Spring 48 is disposed within the open center slots 50a and 50b formed in the handle portions 52a and 52b of each clamping section 42a and 42b, respectively. The free ends 48a and 48b of spring 48 are disposed in exterior cutout sections 54a and 54b of clamping sections 42a and 42b, respectively, to exert a spring biased force pressing the clamping sections 42a and 42b together so that the inward facing, opposing surfaces 42c and 42d of each clamping section 42a and 42b form the cylindrically shaped clamp 42 with a hollow central through passageway 58 (see FIG. 11) formed by the opposing concave surfaces 42e and 42f extending there through and adapted to receive the laser optical fiber 12. Spring 48 provides a spring-loaded force that clamps the two clamping sections 42a and 42b together. The user operates laser optical fiber clamp 42 by applying pressure to the two handle portions 52a and 52b of the clamping sections 42a and 42b so that the clamping sections pivot to an open condition as shown in FIG. 9.

Each clamping section 42a and 42b has an opening 60a and 60b, respectively, through a central portion thereof which receives a rubber tab 62a and 62b (a detailed view is seen in FIG. 9). Each of the rubber tabs 62a and 62b are held in place in the openings 60a and 60b by the free ends 48a and 48b, respectively, of spring 48. When laser optical fiber clamp 42 is assembled, the two rubber tabs 62a and 62b are engaged as shown in FIG. 7 and FIG. 11. Because of the force created by spring 48, rubber tabs 62a and 62b are pressed tightly against each other. In use, the laser optical fiber 12 is disposed within the hollow center 58 and between the rubber tabs 62a and 62b to ensure that the laser optical fiber 12 does not move about, particularly when it is disposed within the device 10 during surgical procedures.

On each end of the clamping sections 42a and 42b are protrusions 64a, 64b, 64c, and 64d (64a-64d). These protrusions 64a-64d are designed to securely mount the laser optical fiber clamp 42 to the storage housing 41 via the front insert 70. The protrusions 64a-64d disposed on opposite ends of cylindrically shaped structure 46 allow either end of the laser optical fiber clamp 42 to be secured within the front insert 70.

As shown in FIG. 7, the front insert 70 is secured at a first end 70a to the open end 41a of the storage housing 41. The front insert 70 has a hollow center bore 72 tending from the first end 70 to a second end 70b. The laser fiber clamp 42 is removably mounted to an opening 74 at the second end 70b, opposite from the storage housing 41. Front insert 70 has a receiver key 76, as shown in FIG. 8, to accommodate either protrusions 64a and 64c, or 64b and 64d on either end of cylindrically shaped structure 46. Once the cylindrically shaped structure 46 is inserted into the receiver key 76 of the front insert 70, the laser optical fiber clamp 42 is firmly secured by rotating it about 90 degrees with respect to the front insert.

The protrusions 56a and 56c, or 56b and 56d secure laser optical fiber clamp 42 within storage housing 41 so that the laser optical fiber clamp 42 is unable to be removed until it is rotated another 90 degrees in either direction to allow protrusions 56a and 56c, or 56b and 56d to disengage from the receiver key 76.

In order to utilize the laser optical fiber clamp 42, the user first squeezes the two handle portions 52a and 52b to place the laser optical fiber clamp 42 in the open position as seen in FIG. 9. Cylindrically shaped structure 46 can open in a range of between 15° and 35° to separate the inward facing, opposing surfaces 42c and 42d from each other. Then, the laser optical fiber 12 is placed within cylindrically shaped structure 46 and the handle portions 52a and 52b are released such that the laser optical fiber 12 is firmly secured between rubber tabs 62a and 62b. Note that the end of the laser optical fiber 12 protruding out from the laser optical fiber clamp 42 is long enough to fit within the storage housing 41 so as to be secured therein. Then, the cylindrically shaped structure 46 is inserted into the front insert 70 so that the laser optical fiber 12 extends into the storage housing 41 a substantial distance as shown in FIG. 7. Then, the cylindrically shaped structure 46 is rotated within the front insert 70 about 90 degrees so that the protrusions 64a and 64c secure the cylindrically shaped structure 46 within the receiver key 76. Once the clamp 42 is secured within the front insert 70, the clamp cannot be opened.

While the laser optical fiber clamp 42 is shown and described to be used in combination with the storage housing 41, it is also within the terms of the invention to use it by itself in various applications where an laser optical fiber needs to be secured.

Referring to FIGS. 12 and 13, there is shown another embodiment device 100 for temporarily storing a laser optical fiber 12 (hereafter "device"). Note that device 100 performs the same functions as device 10 but includes a few additional features as discussed hereinafter. Device 100 is designed as a laser optical fiber storage system for temporarily storing a free end section 12a of the elongated flexible laser optical fiber 12. Device 100 includes a storage housing 114 having an open end 116. As with the device 10, by temporarily disposing the free end 12a of laser optical fiber 12 in storage housing 114, the free end is protected from any potential source of contamination or potential breakage, and any accidentally discharged laser light from the laser optical fiber is safely contained within the storage housing.

There are a number of ring shaped protrusions 118 that can be attached to the top, side, and bottom of device 100 and used to attach device 100 to a patient by any other suitable attachment means.

The device 100 is preferably constructed as a storage housing 114 formed of two hollow storage housing sections 114a and 114b, which are the mirror image of each other. When housing sections 114a and 114b are joined together as shown in FIG. 12, the ribs 115a and 115b formed in the housing sections 114a, 114b, respectively, engage each other and form a spiral shaped channel 119. The housing sections 114a and 114b can be joined together by any means such as screws. The storage housing 114 can be constructed of a variety of materials, such as but not limited to, for example, plastic, silicone, polymers and aluminum.

The open end 116 of housing 114 has a threaded section 120 which is in communication with a funnel shaped, interior section 122, as seen in FIG. 14. The funnel shaped interior section 122 has an outlet opening 122a aligned with the open end 126a of the passageway 126 extending through an elongated flexible tube 128 which is secured within the spiral shaped channel 119.

A laser optical fiber clamp 123 is provided in the opening 126 to the housing 114 to ensure that laser optical fiber 12 remains in place within the storage housing 114 during the use of the device 100 in the midst of a surgical procedure. The clamping mechanism of laser optical fiber clamp 123 prevents movement of a clamped laser optical fiber 12 by a pulling force of between two and five pounds.

Clamp 123 incldes a threaded cap 124 having a bore 130 (see FIG. 13) extending there through and a thread 132 extending outward from a cylindrical section 124a to threadedly mount the clamp within the threaded section 120. One end 130a of bore 130 forms a wide mouth while the opposite end 130b of the bore 130 opens to the passageway 136 extending through a flexible tube 138 which can be constructed of a material that is designed to be laser energy impermeable, such as an elastomeric, or silicone rubber. The flexible tube 138 is disposed between a pair of cantilevered, compliant arms 140a, 140b which project outward from the end 124b of the cylindrical section 124a. Compliant arms 140a, 140b can have a concave inner surface 142a, 142b which receives the flexible tube 138 as seen in FIG. 15. Each of the compliant arms 140, 140b can have a slot 144a, 144b which provides an active hinge to enable the compliant arms to move towards each other and compress the tube 138 as shown in FIG. 15 and described hereinafter.

As shown in FIG. 14, an optical fiber 12 can be inserted into the bore 130 extending through clamp 123. The wide mouth section 130a, as seen in FIG. 13, guides the fiber into the bore. When the fiber exits bore 130 through end 130b, it is directed into the bore 136 through flexible tube 138, see FIG. 13. After the fiber is inserted through the cap 123 and the tube 138, the walls of the funnel shaped interior section 122 direct the fiber through outlet opening 122a.

A flexible disk 150 having a plurality of intersecting slits 152 therethrough being disposed between the outlet opening 122a of the funnel shaped interior section 122 and the inlet 126a of the through passageway 126 through the flexible tube 128. The flexible disk 150 can be removably held in place by ribs 115. The purpose of the flexible disk 150 is to enable the user to feel the presence of the fiber 12 as it moves through the opening formed by the flexing of the intersecting slits 152.

The elongated flexible tube 128 has an outer diameter of about 1.7 cm, an inner passageway 126 has a diameter of about 0.1 cm to about 1 cm, and the wall thickness of the tube 128 can be about 0.3 cm to about 1 cm.

Referring to FIGS. 13 and 14, there is shown one side 114b of the storage housing 114. Housing 114 is configured to insert and retain the free end section 12a of the laser optical fiber 12 in a coiled configuration within silicone rubber tube 128 so as to enable the complete removal of the free end section of the laser optical fiber there from.

There are a plurality of spaced ribs 115b that extend from mating side section 114b, as shown in FIGS. 13 and 14, and a matching plurality of spaced of ribs 115a (not shown) extending outward from the inner side of side section 114a. Each of the ribs 115a and 115b has a semi-circular cutout 117a (not shown) and 117b, respectively, sized to accommodate the tube 128, described hereinafter, so when the two sides 114a and 114b are secured together, the tube 128 is enclosed by a circular openings formed by semicircular cutouts 117a and 117b formed when the matching pairs of ribs 115a and 115b engage each other. The circular openings form a spiral shaped pathway to configure the elongated flexible tube 128 in a coiled configuration as shown in FIG. 13.

The elongated flexible tube 128 is selected to be substantially non-burnable when exposed to a medical laser beam fired through the laser optical fiber 12. Moreover, the tube 128 is able to resist burn-through when exposed to a medical laser beam for at least a desirable time interval of about 1 second to about five minutes.

While elongated flexible tube 28 can be constructed of any desirable material able to resist burn-through when exposed to a medical laser beam for at least the desirable time interval, a preferred material is silicone, such as platinum cured silicone rubber tubing.

As with the tube 28 of the first embodiment, the inner diameter of the tube 128 is reduced by squeezing the tube 128. This could be accomplished by creating a section of the circular openings formed by semicircular cutouts 117a and 117b which are sized to squeeze the inner diameter of tube 128 at section 128a into a smaller diameter.

As noted before, the purpose of reducing the inner diameter of the tubing 128 is to catch the end 12b of a larger laser optical fiber 12 extending through the section 128a as generally shown in FIG. 14. With a laser optical fiber 12 having a smaller diameter, the fiber will more easily pass through the necked down section of the tube and continue on down the tube as described hereinafter.

The end of section 128b of the tube 128 can be closed by any means such as a plug (not shown) or by squeezing the inner diameter of tube 128 at section 128b into a smaller diameter by reducing the diameter of the circular openings formed by semicircular cutouts 117a and 117b.

When a thinner optical filament passes through section 128a of tube 128, it is possible that it will go as far as the end section 128b. In the event of an accidental discharge of laser light, the light will not be go through the closed end 128b and therefore, the laser light will not escape from the housing 114.

In operation, such as during a medical procedure, a laser optical fiber, such as laser optical fiber 12, is secured at one end 12a to a laser energy source 43 (see FIG. 7). The opposite end 12b of the laser optical fiber is typically connected to a surgical instrument (not shown). However, when the free end 12b of laser optical fiber 12 is disconnected from the surgical instrument, while the opposite end 12a is still secured to the laser energy source 43, the free end 12b is loose and free to move about during surgical procedures. This freedom of movement can easily lead to the laser optical fiber 12 being broken or losing its sterility. Further, as discussed hereinbefore, the free laser optical fiber 12 can cause a significant injury to a patient or medical personnel in the event that the laser optical fiber is accidently fired off.

It would be desirable to secure the free end 12b of laser optical fiber 12 at some location so that the movement of the free end can be controlled. The combination of the storage housing 114 and the laser optical fiber clamp 123 alleviates this issue, as it can be secured at any location on the laser optical fiber 12 to thereby stabilize the fiber and prevent its movement from storage housing 114. This stabilization of laser optical fiber 12 is of great benefit to medical personnel conducting the surgical procedures.

As shown in FIG. 14, an optical fiber 12 can be inserted into the bore 130 extending through clamp 123. The wide mouth section 130a, as seen in FIG. 13, guides the fiber into the bore. When the fiber exits bore 130 through end 130b, it is directed into the bore 136 through flexible tube 138, see FIG. 13. After the fiber is inserted through the threaded cap 124 and the tube 138, the walls of the funnel shaped interior section 122 direct the fiber through outlet opening 122a. Once the fiber is securely within the housing 114, which can be determined by the feel of the fiber going through the disk 150 and then contacting the section 128a of the tube 128 or after the fiber moves further into the tube 128 as far as the end 128a, the threaded cap 124 is rotated from the position shown in FIG. 14 wherein the compliant arms 140, 140b are spaced from each other so that the fiber can go through the tube 138. Then, when the fiber 12 is inserted to the desired location, the threaded cap is rotated about 90 degrees so that the cantilevered compliant arms 140a, 140b are brought together by the cam action of the arms against the walls of the funnel shaped interior section 122 as shown in FIG. 15. The compliant arms squeeze the tube 138 and grip or clamp the optical fiber in place. The clamping mechanism of laser optical fiber clamp 123 prevents movement of a clamped laser optical fiber 12 by a pulling force of between two and five pounds.

When the operator wants to remove the fiber, the threaded cap 123 is rotated in an opposite direction for about 90 degrees so that the cantilevered compliant arms 140a, 140b are separated from each other as shown in FIG. 14 and the fiber 12 can be withdrawn without causing any damage to the fiber.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A laser optical fiber storage device for temporarily storing a free end of an elongated flexible laser optical fiber, comprising:
   a storage housing having an open end;
   an elongated flexible tube disposed within the storage housing adapted to receive the elongated flexible laser optical fiber so as to prevent laser light from escaping the storage housing; and
   a restrictor within the storage housing to reduce the inner diameter of the elongated flexible tube.

2. The laser optical fiber storage device of claim 1 further including a funnel disposed within the open end of the storage housing to guide the elongated flexible laser optical fiber into the storage housing.

3. The laser optical fiber storage device of claim 2 wherein an access passageway through the funnel has a smaller diameter than the passageway through elongated flexible tube to enable the elongated flexible laser optical fiber to enter the passageway through elongated flexible tube.

4. The laser optical fiber storage device of claim 1 wherein the restrictor includes:
   an inner bore to receive tube;
   said inner bore having two outer sections having a diameter corresponding to the outer diameter of the tube and a central section necking down to a smaller diameter than the outer diameter so as to reduce the diameter of the tube and the inner diameter of passageway.

5. The laser optical fiber storage device of claim 1 wherein the restrictor is mounted to the housing.

6. The laser optical fiber storage device of claim 1 wherein the storage housing is formed of two hollow storage housing halves which are the mirror image of each other.

7. The laser optical fiber storage device of claim 6 wherein the two hollow storage housing halves each has a plurality of spaced ribs extending there from and having semicircular cutouts, such that when the two hollow storage housing halves are joined together to form storage housing, pairs of the spaced ribs match up with each other so that the semicircular cutouts of the matching pairs of ribs form a plurality of circular openings with a first diameter that encloses the tube.

8. The laser optical fiber storage device of claim 7 wherein a section of the circular openings has a second diameter smaller than the first diameter to squeeze the tube so as to reduce the diameter of the tube and the inner diameter of passageway.

9. The laser optical fiber storage device of claim 7 wherein the circular openings form a spiral shaped pathway to configure the elongated flexible tube in a coiled configuration.

10. The laser optical fiber storage device of claim 2 wherein a first section of the tube between the funnel and the restrictor has a larger wall thickness than the remainder of the tube to prevent burn through from the laser light emitting from a side-fire optical fiber.

11. The laser optical fiber storage device of claim 10 wherein the first section of the tube is covered by an outer tube.

12. The laser optical fiber storage device of claim 2 wherein the elongated flexible tube is constructed of silicone rubber that is substantially non-burnable when exposed to a laser beam for at least a desirable time interval.

13. The laser optical fiber storage device of claim 1 further including a clamp mounted to the open end of the storage housing.

14. The method for temporarily storing a free end of an elongated flexible laser optical fiber, comprising:
   providing a storage housing having an open end;
   disposing an elongated flexible tube within the storage housing;
   inserting the free end of the elongated flexible laser optical fiber into the elongated flexible tube so as to prevent laser light from escaping the storage housing; and
   reducing the inner diameter of the elongated flexible tube to engage the free end of the optical fiber.

15. The method of claim 14 further including guiding the elongated flexible laser optical fiber into the elongated flexible tube through a funnel.

16. The method of claim 15 further including configuring the elongated flexible tube in the storage housing in a coiled configuration.

17. The method of claim 15 further including providing a first section of the flexible tube between the funnel and a section of reduced inner diameter with a larger wall thickness than the remainder of the tube to prevent burn through from the laser light emitting from a side-fire optical fiber.

18. The method of claim 15 further including constructing the flexible tube of silicone rubber that is substantially non-burnable when exposed to a laser beam for at least a desirable time interval.

19. The method of claim 15 further including clamping the elongated flexible laser optical fiber to the open end of the storage housing.

20. A laser optical fiber storage device for temporarily storing a free end of an elongated flexible laser optical fiber, comprising:
   a storage housing having an open end;
   an elongated flexible tube disposed within the storage housing adapted to receive the elongated flexible laser optical fiber so as to prevent laser light from escaping the storage housing; and
   a laser fiber clamp mounted to the open end adapted to secure the laser optical fiber within the flexible tube.

21. The laser optical fiber storage device of claim 20 wherein the laser fiber clamp further includes:
   a cylindrically shaped structure formed of two clamping sections with a hollow central bore therethrough;
   the two clamping sections are pivotally secured together by a spring to exert a spring biased force pressing the clamping sections;
   the two rubber tabs located in openings through the two clamping sections are held in place by free ends of the spring; and
   handle portions of each clamping section adapted to pivotally open the clamping sections whereby the rubber tabs are spaced from each other.

22. The laser optical fiber storage device of claim 21 wherein protrusions are disposed on opposite ends of the cylindrically shaped structure allow either end of the laser fiber clamp to be secured within a front insert secured at a first end within the open end of the storage housing.

23. The laser optical fiber storage device of claim 22 wherein:
   the front insert has a hollow center there through an opening at the second end; and
   a receiver key within the second end to which protrusions of the cylindrically shaped structure are removably mounted.

24. The laser optical fiber storage device of claim 20 further including a restrictor within the storage housing to reduce the inner diameter of the elongated flexible tube.

25. The laser optical fiber storage device of claim 20 wherein the open end of housing has a threaded section which is in communication with a funnel shaped, interior section having an outlet opening aligned with the open end of the passageway extending through elongated flexible tube.

26. The laser optical fiber storage device of claim wherein the laser fiber clamp includes:
   a threaded cap having a bore extending there through and being threadedly mounted within the threaded section;
   a pair of cantilevered, compliant arms which project outward from an end of the threaded cap;
   a flexible tube having a passageway disposed between compliant arms, the passageway being adapted to receive the elongated flexible laser optical fiber having the free end temporarily stored within the laser optical fiber storage device.

27. The laser optical fiber storage device of claim 26 further including a flexible disk having a plurality of intersecting slits therethrough, the flexible disk being disposed between the outlet opening of the funnel shaped, interior section and the inlet of the passageway through the flexible tube.

28. The method of temporarily storing a free end of an elongated flexible laser optical fiber, comprising:
   providing a storage housing having an open end;
   mounting a laser fiber clamp to the open end of the storage housing;
   securing an elongated flexible laser optical fiber within the laser fiber clamp whereby the elongated flexible laser optical fiber is disposed within the storage housing so as to prevent laser light from escaping the storage housing.

29. The method of claim 28 further including:
   inserting the laser fiber clamp into a front insert disposed within the open end of the storage housing; and
   rotating the laser fiber clamp in a first direction to secure the clamp within the front insert.

30. The method of claim 29 further including:
   rotating the laser fiber clamp in a second direction to disengage the clamp from the front insert;
   withdrawing the laser fiber clamp from within the front insert; and opening the clamp and removing the elongated flexible laser optical fiber there from.

31. The method of claim 28 further including:
   providing the storage housing with an open end having a threaded section communicating with a funnel shaped, interior section having an outlet opening;
   disposing a threaded cap of the laser fiber clamp within the threaded section of the open end;

providing spaced compliant arms on an end of the threaded cap so as to engage the walls of the funnel shaped, interior section;

disposing a flexible tube having a bore therethrough between compliant arms;

inserting the optical fiber through the threaded cap, and through the flexible tube into the housing;

rotating the threaded cap in a first direction so the compliant arms are brought together by the cam action of the arms against the walls of the funnel shaped interior section whereby the flexible tube is squeezed so that the optical fiber is clamped in place; and rotating the threaded cap in a second direction so the compliant arms are spaced from each other so that the optical fiber can be withdrawn from the clamp.

32. A laser fiber clamp comprising:

a cylindrically shaped structure formed of two clamping sections with a hollow central bore there through;

the two clamping sections are pivotally secured together by a spring to exert a spring biased force pressing the clamping sections;

the two rubber tabs located in openings through the two clamping sections are held in place by free ends of the spring; and handle portions of each clamping section adapted to pivotally open the clamping sections whereby the rubber tabs are spaced from each other.

33. The laser fiber clamp of claim 32 further including protrusions disposed on opposite ends of the cylindrically shaped structure allowing either end of the laser fiber clamp to be secured within a front insert of a storage housing.

\* \* \* \* \*